United States Patent [19]

Fumeaux et al.

[11] Patent Number: 5,338,741
[45] Date of Patent: Aug. 16, 1994

[54] 1-HYDROXYALKYLXANTHINES AND MEDICAMENTS CONTAINING THEM

[75] Inventors: René Fumeaux, La Tour-de-Peilz; Georges Philippossian, Lausanne, both of Switzerland

[73] Assignee: Nestec S.A., Vevey, Switzerland

[21] Appl. No.: 998,876

[22] Filed: Dec. 29, 1992

Related U.S. Application Data

[63] Continuation of Ser. No. 823,019, Jan. 15, 1992, which is a continuation of Ser. No. 453,026, Dec. 21, 1989, abandoned, which is a continuation of Ser. No. 109,957, Oct. 19, 1987, abandoned.

[30] Foreign Application Priority Data

Oct. 27, 1986 [CH] Switzerland ............ 4253/86-8

[51] Int. Cl.$^5$ .................... A61K 31/52; C07D 473/06
[52] U.S. Cl. ........................ 514/262; 544/267
[58] Field of Search .................. 514/262; 544/267

[56] References Cited

U.S. PATENT DOCUMENTS

| | | | |
|---|---|---|---|
| 2,517,410 | 8/1950 | Papesch | 544/267 |
| 3,065,234 | 11/1962 | Klingler | 544/267 |
| 4,108,995 | 8/1978 | Mohler et al. | 514/263 |
| 4,469,698 | 9/1984 | Philippossian et al. | 514/263 |
| 4,515,795 | 5/1985 | Hinze et al. | 514/263 |
| 4,548,818 | 10/1985 | Kjellin et al. | 514/263 |
| 4,833,146 | 5/1989 | Gebert et al. | 514/263 |

FOREIGN PATENT DOCUMENTS 1211333 3/1960 France.

OTHER PUBLICATIONS

Erjavec et al, Arch. Int. Pharmacodynamics 155, p. 251 (1965).
Physicians' Desk Reference, Medical Economics Co., Inc., Oradell, N.J., (1988), pp. 1055–1056, 2227–2229.
Cardiovascular Pharmacology, 2nd ed., Antonaccio, ed., Raven Press, New York, 1984, Francis, et al., pp. 295–327.
Martindale, "The Extra Pharmocopeia", 29th ed, Reynolds, ed., The Pharmaceutical Press, London, 1989, Milrinone entry.
The Merck Index, 8th ed., (1968) pp. 60 and 1034.
Hinze, et al., Arzneim.-Forsch. (Drug Res.), vol. 22, No. 7, pp. 1144–1151 (1972).
Hinze, Chemical Abstracts, vol. 78(5):23834z (1972).

*Primary Examiner*—Mark L. Berch
*Attorney, Agent, or Firm*—Vogt & O'Donnell

[57] ABSTRACT

Compounds, physiologically acceptable salts of the compounds and pharmaceutical compositions containing the compounds or the salts are provided wherein the compounds have a formula of:

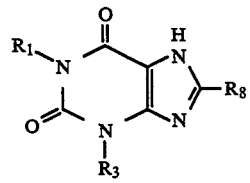

in which $R_1$ is a $C_2$–$C_5$ ω-hydroxy-n-alkyl group or a $C_3$–$C_5$ (ω-1)-hydroxy-n-alkyl group, $R_3$ is a $C_1$–$C_4$ alkyl group, $R_8$ is H, methyl, or ethyl and the sum of the carbon atoms in $R_1$ and $R_3$ is between 4 and 9 and provide inotropic (cardiotonic) activity.

2 Claims, No Drawings

1-HYDROXYALKYLXANTHINES AND MEDICAMENTS CONTAINING THEM

This application is a continuation application of application Ser. No. 07/823,019, filed Jan. 15, 1992, which, in turn, is a continuing application of application Ser. No. 07/453,026, filed Dec. 21, 1989, now abandoned, which in turn, is a continuing application of application Ser. No. 07/109,957, filed Oct. 19, 1987, now abandoned.

BACKGROUND OF THE INVENTION

This invention relates to a new class of xanthines, namely 1-hydroxyalkyl xanthines, to processes for their preparation and to a medicament containing them.

E P 39780 relates to 1,3- or 1,3,8-substituted xanthines showing sedative and anxiolytic properties. These compounds were developed with a view to enhancing or making more specific certain therapeutically useful physiological effects of natural xanthines, such as caffeine or theophylline. Despite their undeniable neuroleptic and anxiolytic character, the compounds according to the abovementioned patent show side effects, particularly on the cardiovascular function. By contrast, the cardiostimulant activity of these compounds, taken on its own, opened up a new channel of investigation in that direction.

DESCRIPTION OF THE INVENTION

The present invention relates to a new class of xanthines, namely 1-hydroxyalkyl xanthines, which show in particular cardiovascular activity. The compounds according to the invention are xanthines corresponding to the following general formula

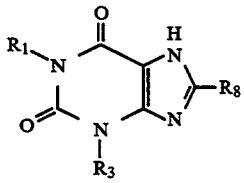

(I)

in which $R_1$ is a $C_2$–$C_5$ ω-hydroxy-n-alkyl group or a $C_3$–$C_5$ (ω-1)-hydroxy-n-alkyl group, $R_3$ is a $C_1$–$C_4$ alkyl group, $R_8$ is H, methyl or ethyl and the sum of the carbon atoms in $R_1$ and $R_3$ is between 4 and 9, or physiologically acceptable salts thereof.

More precisely, the following compounds are more specifically part of the invention:
1-(2-Hydroxyethyl)-3-propyl xanthine,
1-(2-Hydroxyethyl)-3-isobutyl xanthine,
1-(2-Hydroxyethyl)-3-isobutyl-8-methyl xanthine,
1-(2-Hydroxypropyl)-3-propyl xanthine,
1-(2-Hydroxypropyl)-3-propyl-8-methyl xanthine,
1-(2-Hydroxypropyl)-3-butyl xanthine,
1-(3-Hydroxypropyl)-3-propyl xanthine,
1-(3-Hydroxypropyl)-3-propyl-8-methyl xanthine,
1-(3-Hydroxypropyl)-3-propyl-8-ethyl xanthine,
1-(3-Hydroxypropyl)-3-butyl xanthine,
1-(3-Hydroxypropyl)-3-isobutyl xanthine,
1-(3-Hydroxypropyl)-3-isobutyl-8-methyl xanthine,
1-(3-Hydroxybutyl)-3-methyl xanthine,
1-(3-Hydroxybutyl)-3-ethyl xanthine,
1-(3-Hydroxybutyl)-3-ethyl-8-methyl xanthine,
1-(3-Hydroxybutyl)-3-propyl xanthine,
1-(3-Hydroxybutyl)-3-isobutyl xanthine,
1-(4-Hydroxybutyl)-3-ethyl xanthine,
1-(4-Hydroxybutyl)-3-propyl xanthine,
1-(4-Hydroxybutyl)-3-propyl-8-methyl xanthine,
1-(4-Hydroxybutyl)-3-butyl xanthine,
1-(4-Hydroxybutyl)-3-isobutyl-8-methyl xanthine,
1-(4-Hydroxypentyl)-3-methyl xanthine
1-(4-Hydroxypentyl)-3-Propyl xanthine,
1-(5-Hydroxypentyl)-3-methyl xanthine,
1-(5-Hydroxypentyl-3-propyl xanthine and
1-(5-Hydroxypentyl)-3 -propyl-8-methyl xanthine.

Physiologically acceptable salts of the compounds corresponding to general formula (I) are understood to be the salts which these compounds form with pharmaceutically acceptable bases. The salts in question are salts of which the cations are harmless with respect to animal organisms and do not produce any side effects in therapeutic doses. Salts such as these include the salts of alkali metals, such as sodium, potassium, pharmaceutically acceptable salts of ammonium and amines known to the expert. These salts are prepared by heating the compound corresponding to general formula (I) in the presence of the appropriate base and in the presence or absence of a solvent, preferably followed by recrystallization.

The compounds according to the invention are prepared by one of the following processes:

A) A uracil corresponding to the following formula

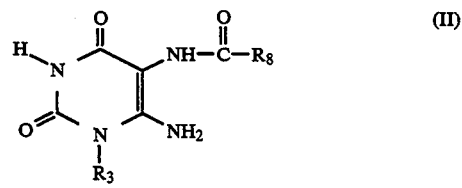

(II)

is reacted with an alkylating agent of the formula $R_1$—X, where $R_1$, $R_3$ and $R_8$ are as defined in general formula (I), except that $R_1$ is not ω-hydroxybutyl, and where X is a halogen atom, preferably bromine, or monosulfate or disulfate or p-toluenesulfonate, in a solvent suitable for al 1 the reactants, such as for example dimethylformamide (DMF), dimethylsulfoxide (DMSO) or hexamethylphosphorotriamide (HMPT), at a temperature in the range from 20° to 40° C. and in the presence of an alkali metal hydroxide, for example sodium hydroxide in solid form. The reaction is preferably carried out in DMF at 20° C. in accordance with the following scheme:

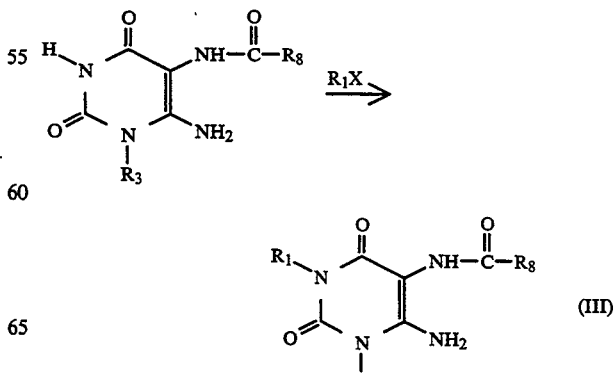

The product corresponding to general formula (III) is then cyclized at 20° to 100° C. in an alkali metal hydroxide solution in accordance with the following reaction scheme:

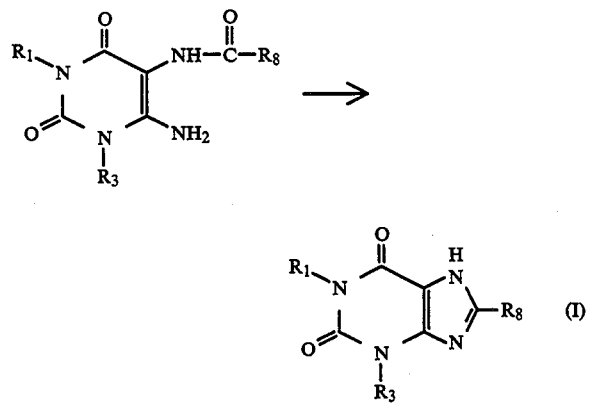

Although it is possible to isolate the derivative of general formula (III), it is preferred to carry out cyclization directly without isolating or purifying the derivative in question. To this end, the reaction medium is neutralized and the solvent evaporated, after which the residue is dissolved in an alkali hydroxide solution and the resulting solution heated to reflux temperature.

B) In a variant of this process, the uracil (II) is alkylated with agent containing a function which may be converted into a hydroxyl group, for example a —COO—$R_4$ function, in accordance with the following reaction scheme:

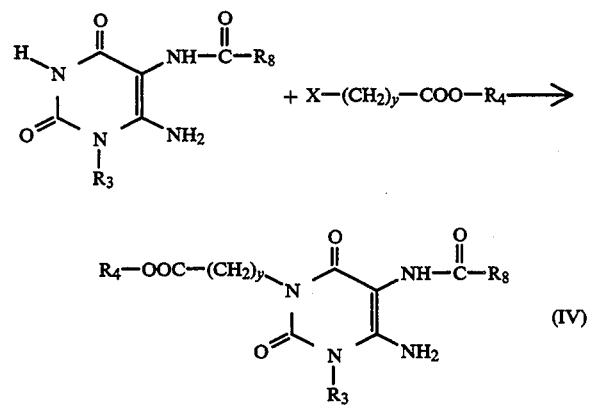

in which $R_3$, $R_8$ and X are as defined above, y is a number of from 1 to 4 and $R_4$ is an alkyl group. This alkylation reaction is carried out in the same way as for A) in a solvent suitable for all the reactants, such as DMF, DMSO or HMPT, at a temperature of from 20° to 40° C. and in the presence of an alkali metal hydroxide in solid form. The alkylation step is followed by cyclization and simultaneous hydrolysis of the ester (IV) at 20° to 100° C. in an alkali metal hydroxide solution in accordance with the following reaction scheme:

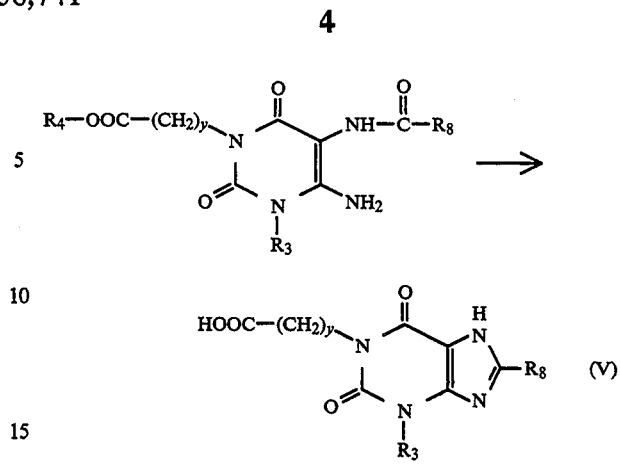

Although the acid (V) may be directly reduced to alcohol, it is preferred to re-esterify the acid (V) with an alcohol, such as methanol, ethanol or propanol, under reflux to obtain the corresponding ester which is then reduced in known manner, for example in the presence of LiAlH$_4$ in THF, to obtain the following product according to the invention:

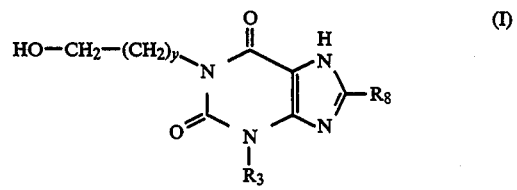

Accordingly, it can be seen that ω-hydroxyalkyl xanthines are always obtained in this second embodiment of the process according to the invention.

C) In a final embodiment of the process according to the invention, (ω-1)-hydroxyalkyl xanthines are prepared by alkylation of the uracil (II)

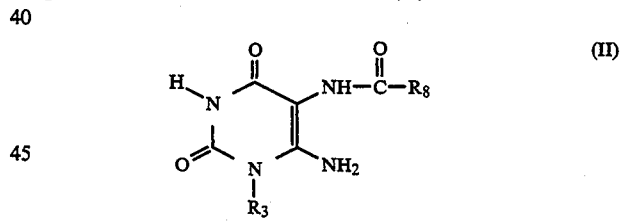

with an alkylating agent of the formula R5X, where $R_3$, $R_8$ and X are as defined above and $R_5$ is a $C_3$-$C_5$ (ω-1)-alkenyl group. The alkylation reaction is carried out under the same conditions as for A) and B), namely in a solvent suitable for all the reactants, such as DMF, DMSO or HMPT, at a temperature in the range from 20° to 40° C. and in the presence of an alkali metal hydroxide in solid form. The intermediate product obtained is then cyclized at 20 to 100° C. in an alkali metal hydroxide solution in accordance with the following reaction scheme:

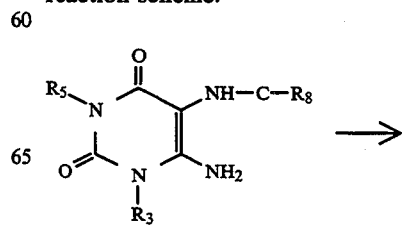

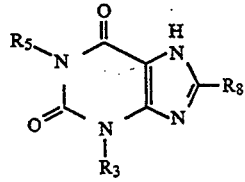

(VI)

below shows the method of preparation and the alkylating agent to be used for 27 compounds according to the invention. Table II shows the melting point and recrystallization solvent for these same 27 compounds and Table III the $^{13}C$ NMR values.

TABLE I

| Xanthine no. | Compound according to the invention | Preparation | Alkylating agent |
|---|---|---|---|
| 1 | 1-(2-Hydroxyethyl)-3-propyl xanthine | Method A | 2-Bromoethanol |
| 2 | 1-(2-Hydroxyethyl)-3-isobutyl xanthine | Method A | 2-Bromoethanol |
| 3 | 1-(2-Hydroxyethyl)-3-isobutyl-8-methyl xanthine | Method A | 2-Bromoethanol |
| 4 | 1-(2-Hydroxypropyl)-3-propyl xanthine | Method C/Variant B | Allyl bromide |
| 5 | 1-(2-Hydroxypropyl)-3-propyl-8-methyl xanthine | Method C/Variant A | Allyl bromide |
| 6 | 1-(2-Hydroxypropyl)-3-butyl xanthine | Method C/Variant B | Allyl bromide |
| 7 | 1-(3-Hydroxypropyl)-3-propyl xanthine | Method A | 3-Bromo-1-propanol |
| 8 | 1-(3-Hydroxypropyl)-3-propyl-8-methyl xanthine | Method A | 3-Bromo-1-propanol |
| 9 | 1-(3-Hydroxypropyl)-3-propyl-8-ethyl xanthine | Method A | 3-Bromo-1-propanol |
| 10 | 1-(3-Hydroxypropyl)-3-butyl xanthine | Method A | 3-Bromo-1-propanol |
| 11 | 1-(3-Hydroxypropyl)-3-isobutyl xanthine | Method A | 3-Bromo-1-propanol |
| 12 | 1-(3-Hydroxypropyl)-3-isobutyl-8-methyl xanthine | Method A | 3-Bromo-1-propanol |
| 13 | 1-(3-Hydroxybutyl)-3-methyl xanthine | Method C/Variant A | 4-Bromo-1-butene |
| 14 | 1-(3-Hydroxybutyl)-3-ethyl xanthine | Method C/Variant A | 4-Bromo-1-butene |
| 15 | 1-(3-Hydroxybutyl)-3-ethyl-8-methyl xanthine | Method C/Variant A | 4-Bromo-1-butene |
| 16 | 1-(3-Hydroxybutyl)-3-propyl xanthine | Method C/Variant A | 4-Bromo-1-butene |
| 17 | 1-(3-Hydroxybutyl)-3-isobutyl xanthine | Method C/Variant A | 4-Bromo-1-butene |
| 18 | 1-(4-Hydroxybutyl)-3-ethyl xanthine | Method B | Ethyl 4-bromobutyrate |
| 19 | 1-(4-Hydroxybutyl)-3-propyl xanthine | Method B | Ethyl 4-bromobutyrate |
| 20 | 1-(4-Hydroxybutyl)-3-propyl-8-methyl xanthine | Method B | Ethyl 4-bromobutyrate |
| 21 | 1-(4-Hydroxybutyl)-3-butyl xanthine | Method B | Ethyl 4-bromobutyrate |
| 22 | 1-(4-Hydroxybutyl)-3-isobutyl-8-methyl xanthine | Method B | Ethyl 4-bromobutyrate |
| 23 | 1-(4-Hydroxypentyl)-3-methyl xanthine | Method C/Variant A | 5-Bromo-1-pentene |
| 24 | 1-(4-Hydroxypentyl)-3-propyl xanthine | Method C/Variant B | 5-Bromo-1-pentene |
| 25 | 1-(5-Hydroxypentyl)-3-methyl xanthine | Method A | 5-Bromo-1-pentanol |
| 26 | 1-(5-Hydroxypentyl)-3-propyl xanthine | Method A | 5-Bromo-1-pentanol |
| 27 | 1-(5-Hydroxypentyl)-3-propyl-8-methyl xanthine | Method A | 5-Bromo-1-pentanol |

The final step comprises hydration of the double bond of $R_5$ by an addition reaction of the Markownikoff type. This addition may be carried out in two ways:

Method A: using dilute sulfuric acid at a temperature of approximately 100° C. over a period of several days.

Method B: by the reductive oxymercuration-demercuration method in the presence of mercury acetate and then $NaBH_4$ (Larock, R.C.: Solvomercuration/-Demercuration Reactions in Organic Synthesis, Springer Verlag, Berlin, 1986, Chap. 2).

The present invention also relates to a pharmaceutical composition containing a compound of general formula (I) in combination with an inert, pharmaceutically acceptable support.

The medicament according to the invention may be made up in various pharmaceutical forms containing the usual excipients or vehicles, such as tablets, capsules, suppositories, solutions, suspensions, and may be administered orally, sublingually, rectally, subcutaneously, intramuscularly, intraveneously or by inhalation.

Before actual examples of the synthesis of the compounds according to the invention are given, Table I

TABLE II

| Xanthine No. | Mp. (°C.) | Recrystallization solvent |
|---|---|---|
| 1 | 178-179 | Acetone |
| 2 | 200-202 | Acetone |
| 3 | 227-229 | Chloroform |
| 4 | 150-152 | Chloroform |
| 5 | 196-197 | Methanol |
| 6 | 157-158 | Water |
| 7 | 145-146 | Methanol |
| 8 | 221-222 | Methanol |
| 9 | 196-198 | Water |
| 10 | 111-112 | Water |
| 11 | 159-160 | Acetone |
| 12 | 248-250 | Ethanol |
| 13 | 200-201 | Acetone |
| 14 | 217-218 | Water |
| 15 | 212-213 | Water |
| 16 | 163-164 | Acetone |
| 17 | 141-142 | Acetone |
| 18 | 207-208 | Water |
| 19 | 173-174 | Acetone |
| 20 | 192-193 | Water |
| 21 | 122-123 | Acetone |
| 22 | 211-212 | Methanol |
| 23 | 180-181 | Acetone |
| 24 | 153-154 | Acetone |
| 25 | 190-191 | Water |
| 26 | 151-152 | Water |
| 27 | 184-185 | Dioxane |

TABLE III

| | $^{13}C$-NMR values (δ ppm; solvent:DMSO-$d_6$; temperature: ambient, except *: 80° C.) | | | | | | | |
|---|---|---|---|---|---|---|---|---|
| | Purine ring | | | | | Substituents | | |
| Xanthine no. | C-2 | C-4 | C-5 | C-6 | C-8 | R-1 | R-3 | R-8 |
| 1 | 150.8 | 147.7 | 106.5 | 154.4 | 140.4 | 42.6 57.9 | 44.4 20.8 10.9 | — |
| 2 | 151.0 | 147.9 | 106.5 | 154.4 | 140.3 | 42.7 57.9 | 49.9 26.9 19.8(2x) | — |
| 3 | 151.0 | 148.2 | 106.1 | 153.8 | 150.3 | 42.5 57.9 | 49.8 26.8 19.7(2x) | 14.1 |
| 4 | 151.0 | 147.7 | 106.6 | 154.6 | 140.5 | 47.5 63.7 20.9 | 44.4 20.9 10.9 | — |
| 5 | 151.0 | 147.9 | 106.2 | 154.0 | 150.4 | 47.3 63.6 20.9 | 44.4 20.9 10.9 | 14.2 |

TABLE III-continued

13C-NMR values (δ ppm; solvent:DMSO-d6; temperature: ambient, except *: 80° C.)

| Xanthine no. | Purine ring | | | | | Substituents | | |
|---|---|---|---|---|---|---|---|---|
| | C-2 | C-4 | C-5 | C-6 | C-8 | R-1 | R-3 | R-8 |
| 6 | 151.0 | 147.6 | 106.6 | 154.5 | 140.4 | 47.5 63.7 20.9 | 42.6 29.6 19.3 13.5 | — |
| 7 | 150.6 | 147.6 | 106.5 | 154.2 | 140.5 | 38.4 31.0 58.8 | 44.4 20.8 10.9 | — |
| 8 | 150.7 | 147.9 | 106.2 | 153.8 | 150.5 | 38.3 31.1 58.9 | 44.4 20.9 10.9 | 14.2 |
| 9 | 150.7 | 147.8 | 106.2 | 153.9 | 155.4 | 38.3 31.1 58.9 | 44.3 20.8 10.9 | 21.7 12.2 |
| 10 | 150.7 | 147.6 | 106.6 | 154.3 | 140.5 | 38.4 31.1 58.9 | 42.6 29.6 19.4 13.5 | — |
| 11 | 150.8 | 147.7 | 106.3 | 154.1 | 139.9 | 38.1 30.9 58.7 | 49.7 26.6 19.4(2x) | — |
| 12 | 150.8 | 148.0 | 106.0 | 153.6 | 150.0 | 37.9 30.9 58.6 | 49.5 26.5 19.3(2x) | 13.8* |
| 13 | 150.9 | 147.8 | 106.5 | 154.3 | 140.4 | 38.4 37.2 64.3 23.5 | 29.6 | — |
| 14 | 150.4 | 147.3 | 106.6 | 154.3 | 140.6 | 38.3 37.2 64.3 23.5 | 38.0 13.1 | — |
| 15 | 150.4 | 147.6 | 106.3 | 153.7 | 150.5 | 38.4 37.2 64.3 23.4 | 38.0 13.1 | 14.2 |
| 16 | 150.7 | 147.6 | 106.3 | 154.3 | 140.5 | 38.3 37.2 64.4 23.5 | 44.4 20.8 10.9 | — |
| 17 | 150.8 | 147.9 | 106.4 | 154.2 | 140.3 | 38.4 37.2 64.3 23.4 | 49.8 26.8 19.7(2x) | — |
| 18 | 150.3 | 147.1 | 106.4 | 154.0 | 140.0 | 40.5 24.2 29.7 60.4 | 37.7 12.7 | — |
| 19 | 150.6 | 147.6 | 106.5 | 154.3 | 140.5 | 40.5 24.4 30.0 60.6 | 44.4 20.8 10.9 | — |
| 20 | 150.5 | 147.9 | 106.2 | 153.8 | 150.5 | 40.5 24.5 30.0 60.6 | 44.3 20.9 10.9 | 14.2 |
| 21 | 150.6 | 147.7 | 106.6 | 154.3 | 140.5 | 40.6 24.5 30.0 60.7 | 42.6 29.7 19.4 13.5 | — |
| 22 | 150.8 | 148.0 | 106.0 | 153.6 | 150.0 | 40.2 24.2 29.7 60.5 | 49.6 26.5 19.4(2x) | 13.8* |
| 23 | 150.9 | 147.9 | 106.4 | 154.2 | 140.4 | 40.8 24.2 36.2 65.7 23.5 | 29.6 | — |
| 24 | 150.6 | 147.6 | 106.5 | 154.2 | 140.4 | 40.6 24.1 36.2 65.7 23.5 | 44.4 20.8 10.9 | — |
| 25 | 150.9 | 147.8 | 106.5 | 154.2 | 140.3 | 40.6 27.4 22.9 32.2 60.6 | 29.6 | — |
| 26 | 150.6 | 147.6 | 106.3 | 154.2 | 140.4 | 40.6 27.4 22.9 32.1 60.5 | 44.4 20.8 10.9 | — |
| 27 | 150.5 | 147.9 | 106.1 | 153.7 | 150.5 | 40.5 27.4 22.9 32.2 60.5 | 44.3 20.9 10.9 | 14.2 |

EXAMPLES

The invention is illustrated by the following Examples in which the quantities are by weight, unless otherwise indicated.

EXAMPLE 1

1-(5-hydroxypentyl)-3-propyl-8-methyl xanthine (Method A: xanthine no. 27)

22.6 g (0.1 mole) of 1-propyl-5-acetylamino-6-aminouracil (II) ($R_3$=methyl, $R_8$=methyl) are suspended under nitrogen in 200 ml of anhydrous dimethyl formamide (DMF). 21.7 g (0.13 mole) of 5-bromo-1-pentanol are then added, after which 6 g (0.15 mole) of powder-form solid NaOH are added with stirring in portions of 1 g at a time at intervals of 1 hour. After the third addition, the suspension is completely dissolved. The solution is left standing overnight to complete the reaction. The solvent is evaporated in a rotary evaporator at 40° C./0.1 mm Hg. The oily residue, which is the uracil (III) ($R_1$=5-hydroxypentyl, $R_3$=propyl, $R_8$=methyl), which is not purified, is dissolved in 100 ml of 10% NaOH and the solution heated under reflux for 2 hours. The solution is then cooled in a ice bath and neutralized to pH 5 with acetic acid. The product precipitated is filtered, washed with cold water and then dried in a vacuum oven. The dried product is dissolved in 500 ml of ethanol and the solution is decoloured overnight with active carbon. The product is precipitated by addition of 1 litre of water, filtered and the treatment with active carbon repeated. The dried product is recrystallized twice with 120 ml of dioxane. Yield: 23.5 g (80%); colourless crystals; Mp. 184–185° C.

EXAMPLE 2

1-(4-hydroxybutyl)-3-butyl xanthine (Method B, xanthine no. 21)

11.3 g (0.05 mole) of 1-butyl-5-formylamino-6-aminouracil (II) ($R_1$=butyl, $R_8$=H) are dissolved under nitrogen in 200 ml of DMF. 10.6 ml (0.075 mole) of ethyl 4-bromobutyrate are added, after which 2 g (0.05 mole) of solid powder-form NaOH is added with thorough stirring in portions of 0.5 g at intervals of 1 hour. On completion of the addition, the mixture is left to react overnight. The solvent is then evaporated and the oily residue of (IV) (substituent in the 1-position=$(CH_2)_3COOEt$) is dissolved in 100 ml of 10% NaOH. This solution is then heated under reflux for 0.5 hour and then cooled, neutralized to pH 5 with acetic acid and filtered. The precipitate formed is dried. Yield: 9.2 g (60%) of crude xanthine (V) (substituent in the 1-position=$(CH_2)_3COOH$, $R_3$=butyl, $R_8$=H).

Without purification, the product is esterified under reflux for 5 hours with 200 ml of methanol containing 1 ml of concentrated sulfuric acid. The solution is concentrated to a small volume and 50 ml of water are added. The ester precipitate formed (substituent in the 1-position=$(CH_2)_3$—COOMe) is filtered, washed and dried. Yield: 9 g (93%).

Without purification, this product is dissolved in 200 ml of anhydrous tetrahydrofuran (THF), cooled to between 0° and −10° C. and added dropwise to a solution containing 2.13 g (0.056 mole) of $LiAlH_4$ in 150 ml of anhydrous THF. On completion of the addition, the mixture is left to react for another 2 hours at 0° C., after which the excess $LiAlH_4$ is destroyed by addition of 50 ml of water. The mixture is acidified to pH 2 with concentrated HCl, after which the THF is evaporated. The residual aqueous solution is continuously extracted overnight with dichloromethane. The organic extract is dried and the solvent evaporated. The slightly coloured solid residue (6.1 g) is recrystallized twice from acetone. Yield: 4.6 g (33% from II); colourless crystals; Mp. 122–123° C.

EXAMPLE 3

1-(3-hydroxybutyl)-3-isobutyl xanthine (Method C/Variant A, xanthine no. 17)

11.3 g (0.05 mole) of 1-isobutyl-5-formylamino-6-aminouracil (II) ($R_3$=isobutyl, $R_8$=H) are dissolved in 220 ml of DMF. 8.8 g (0.065 mole) of 4-bromo-1-butene are added, after which 3 g (0.075 mole) of powder-form NaOH are added with stirring in portions of 0.5 g at intervals of 1 hour. The mixture is left standing overnight, after which the solvent is evaporated in vacuo.

The crude residue ($R_5$=3-butenyl) is taken up in 100 ml of 10% NaOH and heated under reflux for 0.5 hour. The solution is then cooled and neutralized to pH 5 with acetic acid, after which the precipitate formed is filtered and dried. 8.5 g of crude solid product (VI) ($R_5$=3-butenyl, $R_3$=isobutyl, $R_8$=H) are obtained. This product is purified by passage through a column of silica (85 g) using chloroform as eluent: 6.5 g of colourless product.

A mixture containing 6 g of the above compound in 100 ml of 20% sulfuric acid is heated at 100° C. for 4 days, cooled and neutralized to pH 5 with 50% KOH. The solution is evaporated to dryness, the residue is taken up in 100 ml of boiling absolute ethanol and the insoluble fraction is filtered. The filtrate is freed from the solvent, leaving a coloured solid residue (6.4 g) which is passed through a column of silica (650 g) eluted with a gradient of chloroform/methanol (0–5% methanol ) . The xanthine is recrystallized twice from acetone. Yield: 4.5 g (33% based on II); Mp. =141–142° C.

EXAMPLE 4

1-(2-hydroxypropyl)-3-butyl xanthine (Method C:Variant B, xanthine no. 6)

16 g (0.050 mole) of mercury (II) acetate are dissolved in 250 ml water. 12.4 g (0.05 mole) of 1-allyl-3-butyl xanthine (prepared as described above from 1-butyl-5-formylamino-6-aminouracil and allyl bromide) dissolved in 250 ml of THF are added dropwise with stirring over a period of 10 minutes. After a few minutes, a precipitate is formed. Stirring is continued for 30 minutes, after which the mixture is cooled in an ice bath. 68 ml of 3 N NaOH are added, followed by the dropwise addition of 60 ml of a freshly prepared 0.5 M solution of $NaBH_4$ in 3 N NaOH. On completion of the addition, stirring is continued for another 15 minutes. The solution is neutralized to pH 4–5 with 6 N HCl (approximately 60 ml), saturated with NaCl and the xanthine extracted with dichloromethane (3×200 ml). The organic extract is dried and the solvent is evaporated: 12.9 g of crude product containing 20% of starting product. The products are separated by passing the mixture through a column of silica using chloroform as eluent for the starting product and chloroform/methanol (95/5) for the hydroxylated xanthine (9.5 g) . The xanthine is recrystallized twice from water: 8.5 g (64%); Mp. 157–158° C.

EXAMPLE 5

The compounds (I) according to the invention have been found to show low toxicity and have little or no effect on the central nervous system. By contrast, they were found to be active in the in vitro tests for inotropic (cardiotonic) activity. Table IV shows the results of these tests.

TABLE (IV)

| Xanthine No. | Cardiotonic activity[1] (minimum effective concentration in μg/ml producing a significant response) |
| --- | --- |
| 1 | 1 |
| 2 | 2.5 |
| 3 | 2 |
| 4 | 3.3 |
| 5 | 0.6 |
| 6 | 4.2 |
| 7 | 1.3 |
| 8 | 4.2 |
| 9 | 2 |
| 10 | 0.4 |
| 11 | 0.7 |
| 12 | 0.5 |
| 13 | 50 |
| 14 | 0.8 |
| 15 | 0.6 |
| 16 | 0.1 |
| 17 | 1.3 |
| 18 | 3.3 |
| 19 | 0.4 |
| 20 | 0.7 |
| 21 | 2 |
| 22 | 25 |
| 23 | 33.3 |
| 24 | 0.7 |
| 25 | 6.7 |
| 26 | 0.2 |
| 27 | 0.3 |

| References | |
| --- | --- |
| Theophylline | 15 |
| Amrinone[2] | 100 |
| Milrinone[2] | 0.5 |
| IBMX[3] | 0.5 |

[1] Measurement of the force of contraction of the isolated and electrically stimulated left auricle of a guinea pig in accordance with Erjavek, F. and Adamic, S., Arch. Int. Pharmacodyn. 155: 251, 1965. A response is considered to be significant when the basic contraction force is increased by more than 40%.
[2] Prior art cardio stimulant medicament.
[3] 1-methyl-3-isobutylxanthine.

We claim:

1. The compound 1-(2-hydroxyethyl)-3-propyl xanthine or a physiologically acceptable salt thereof.

2. A pharmaceutical composition comprising an inert pharmaceutically acceptable excipient and 1-(2-hydroxyethyl)-3-propyl xanthine or a physiologically acceptable salt thereof.

* * * * *